US010220123B2

(12) United States Patent
Monty et al.

(10) Patent No.: US 10,220,123 B2
(45) Date of Patent: Mar. 5, 2019

(54) HAND HELD IRRIGATION AND SUCTION TOOL

(75) Inventors: Charles J. Monty, Milwaukee, WI (US); Philippe A. Capraro, Denver, CO (US); Thomas S. Doig, West Bend, WI (US)

(73) Assignee: Camodo, LLC, West Bend, WI (US)

( * ) Notice: Subject to any disclaimer, the term of this patent is extended or adjusted under 35 U.S.C. 154(b) by 0 days.

(21) Appl. No.: 13/817,958

(22) PCT Filed: Aug. 25, 2011

(86) PCT No.: PCT/US2011/049248
§ 371 (c)(1),
(2), (4) Date: Mar. 14, 2013

(87) PCT Pub. No.: WO2012/027624
PCT Pub. Date: Mar. 1, 2012

(65) Prior Publication Data
US 2013/0165849 A1   Jun. 27, 2013

Related U.S. Application Data

(60) Provisional application No. 61/377,085, filed on Aug. 25, 2010.

(51) Int. Cl.
*A61M 1/00* (2006.01)
*A61M 3/02* (2006.01)

(52) U.S. Cl.
CPC .......... *A61M 1/0064* (2013.01); *A61M 3/022* (2014.02); *A61M 3/0283* (2013.01); *A61M 1/0047* (2013.01)

(58) Field of Classification Search
CPC .............. A61M 1/0039; A61M 1/0041; A61M 1/0047; A61M 1/0064; A61M 3/022; A61M 3/0283; A61M 1/0045; A61M 1/0058
(Continued)

(56) References Cited

U.S. PATENT DOCUMENTS 493,208 A * 3/1893 Cruickshank ................... 604/36
1,223,963 A * 4/1917 Gollomb ........................ 604/36
(Continued)

FOREIGN PATENT DOCUMENTS

DE    1873701    6/1963
EP    0199876    11/1986
(Continued)

*Primary Examiner* — Kami A Bosworth
(74) *Attorney, Agent, or Firm* — Boyle Fredrickson S.C.

(57) ABSTRACT

An irrigation tool that includes a handle configured for grasping by a hand of a user of the tool having a handgrip displaceable using the hand in a manner that selectively controls the rate of flow of irrigation fluid discharged from the tool. The handgrip includes a compressible chamber mounted to the handle via at least one fluid coupling with the chamber compressible by manually squeezing the handgrip to discharge irrigation fluid. The chamber can be provided by a bulb in operable cooperation with a fluid coupling that provides an irrigation fluid flow-modulating control valve arrangement responsive to the magnitude and rate of applied squeezing force. The tool can include an aspirator having a suction passage integrally formed in the handle with a suction control valve operable using the same hand used to control irrigation fluid flow producing a hand-held hand operated combination irrigation and suction tool.

33 Claims, 10 Drawing Sheets

(58) Field of Classification Search
USPC ........ 222/207, 209, 210, 212, 213; 251/342;
604/27, 30, 34, 35, 37, 119, 142, 186,
604/204, 212, 213, 215, 217, 246, 247,
604/256, 36, 214
See application file for complete search history.

(56) References Cited

U.S. PATENT DOCUMENTS

| | | | |
|---|---|---|---|
| 1,314,855 A | 9/1919 | Carpenter | |
| 1,925,230 A | 9/1933 | Buckhout | |
| 2,531,793 A | 11/1950 | Sulek | |
| 3,065,749 A | 11/1962 | Brass | |
| 3,109,426 A | 11/1963 | Noonan et al. | |
| 3,208,145 A | 9/1965 | Turner | |
| 3,398,743 A | 8/1968 | Shalit | |
| 3,474,936 A * | 10/1969 | McDonnell | 222/211 |
| 3,749,090 A | 7/1973 | Stewart | |
| 3,889,675 A | 6/1975 | Stewart | |
| 4,299,221 A | 11/1981 | Phillips et al. | |
| 4,397,640 A | 8/1983 | Haug et al. | |
| 4,430,073 A | 2/1984 | Bemis et al. | |
| 4,502,508 A | 3/1985 | Lester | |
| 4,519,385 A | 5/1985 | Atkinson et al. | |
| 4,526,573 A | 7/1985 | Lester et al. | |
| 4,553,957 A | 11/1985 | Williams et al. | |
| 4,598,698 A * | 7/1986 | Siegmund | A61B 1/12 600/131 |
| 4,662,871 A | 5/1987 | Rafelson | |
| 4,680,026 A | 7/1987 | Weightman et al. | |
| 4,776,840 A | 10/1988 | Freitas et al. | |
| 4,852,551 A | 8/1989 | Opie et al. | |
| 4,941,872 A | 7/1990 | Felix et al. | |
| 5,019,054 A | 5/1991 | Clement et al. | |
| 5,125,910 A | 6/1992 | Freitas | |
| 5,145,367 A | 9/1992 | Kasten | |
| 5,147,292 A * | 9/1992 | Kullas et al. | 604/34 |
| 5,195,959 A | 3/1993 | Smith | |
| 5,203,769 A | 4/1993 | Clement et al. | |
| 5,219,348 A | 6/1993 | Buess et al. | |
| 5,224,929 A | 7/1993 | Remiszeewski | |
| 5,230,704 A | 7/1993 | Moberg | |
| 5,244,459 A | 9/1993 | Hill | |
| 5,247,966 A | 9/1993 | Stevens et al. | |
| 5,269,768 A | 12/1993 | Cheung | |
| 5,279,549 A | 1/1994 | Ranford | |
| 5,295,956 A | 3/1994 | Bales | |
| 5,312,373 A | 5/1994 | Freitas | |
| 5,320,328 A | 6/1994 | Decloux et al. | |
| 5,322,503 A | 6/1994 | Desai | |
| 5,338,313 A | 8/1994 | Mollenauer et al. | |
| 5,347,992 A | 9/1994 | Pearlman et al. | |
| 5,470,305 A | 11/1995 | Arnett et al. | |
| 5,484,402 A | 1/1996 | Saravia | |
| 5,490,836 A | 2/1996 | Desai | |
| 5,556,387 A | 9/1996 | Mollenauer et al. | |
| 5,609,573 A | 3/1997 | Sandock | |
| 5,692,729 A | 12/1997 | Herhen | |
| 5,738,648 A | 4/1998 | Lands et al. | |
| 5,830,214 A | 11/1998 | Flom | |
| 6,099,494 A | 8/2000 | Henniges et al. | |
| 6,213,970 B1 | 4/2001 | Nelson et al. | |
| 6,364,853 B1 | 4/2002 | French et al. | |
| 6,464,498 B1 | 10/2002 | Pond | |
| 6,620,132 B1 * | 9/2003 | Skow | 604/131 |
| 6,623,445 B1 | 9/2003 | Nelson et al. | |
| 6,907,879 B2 | 6/2005 | Drinan et al. | |
| 6,918,764 B2 | 7/2005 | Ito et al. | |
| 6,932,788 B2 | 8/2005 | Kamiyama et al. | |
| 6,958,058 B1 | 10/2005 | Hunter, Sr. | |
| 7,241,294 B2 | 7/2007 | Reschke | |
| 7,297,133 B2 | 11/2007 | Nelson et al. | |
| 7,540,873 B2 | 6/2009 | Bayat | |
| 7,597,686 B2 | 10/2009 | MacMillan et al. | |
| 7,727,177 B2 | 6/2010 | Bayat | |
| 7,967,774 B2 | 6/2011 | Bayat | |
| 8,708,200 B2 * | 4/2014 | Nilsson | 222/207 |
| 2006/0212056 A1 | 9/2006 | Salvadori et al. | |
| 2007/0106204 A1 | 5/2007 | Fedina et al. | |

FOREIGN PATENT DOCUMENTS

| | | |
|---|---|---|
| GB | 1602277 | 11/1981 |
| JP | 2001-333988 | 12/2001 |
| KR | 10-2009-0131089 | 12/2009 |
| WO | 1986004247 | 7/1986 |
| WO | 2005027740 | 3/2005 |

* cited by examiner

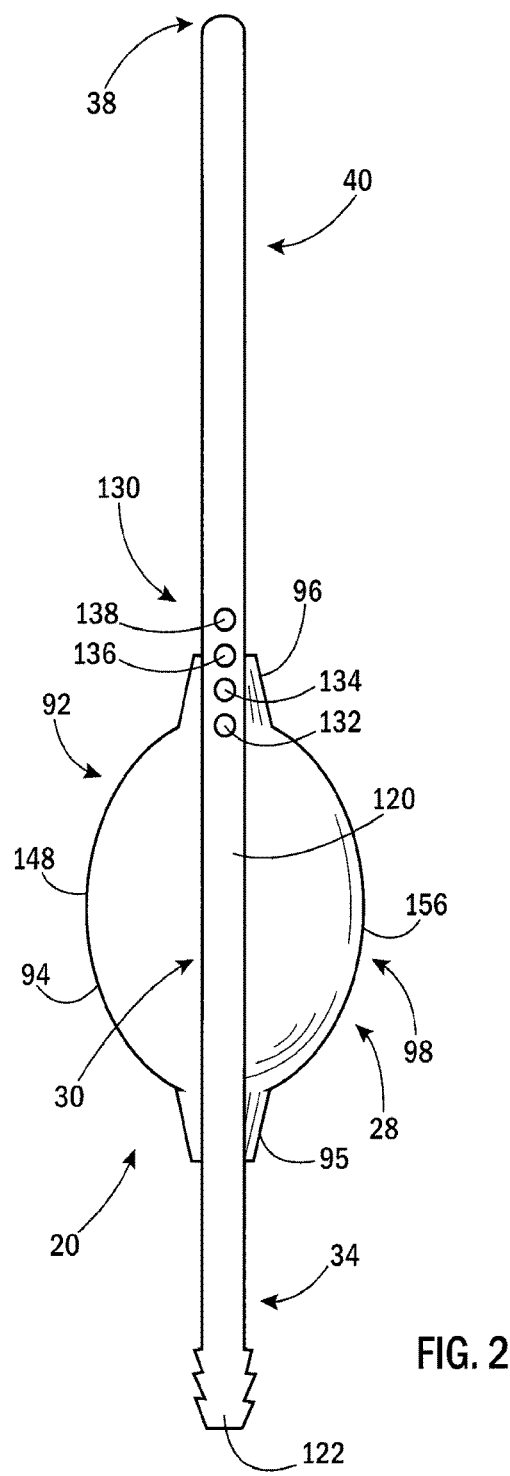
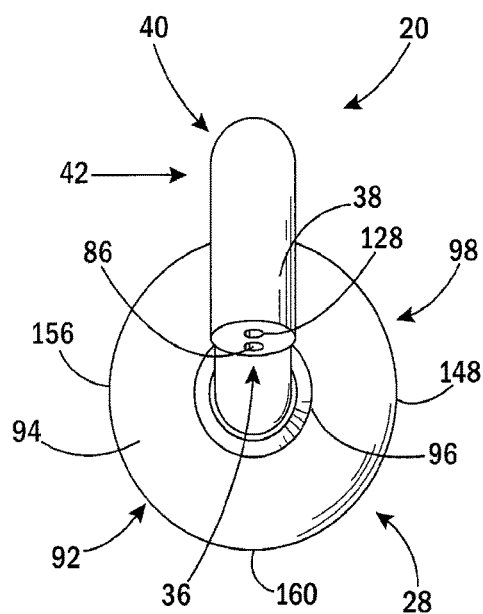
FIG. 2
FIG. 3

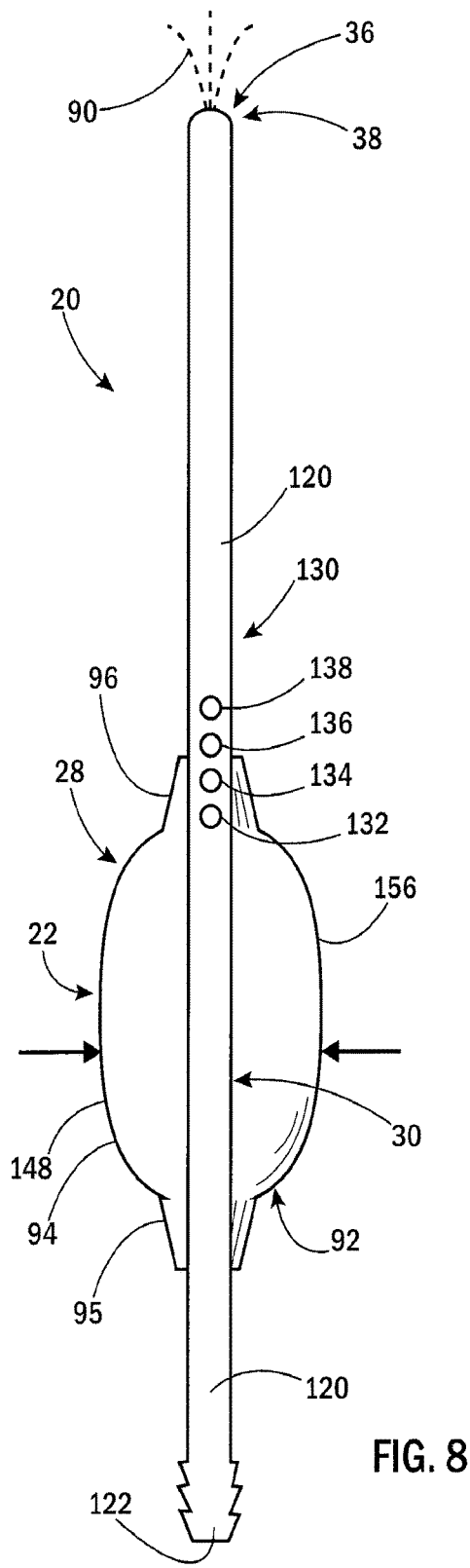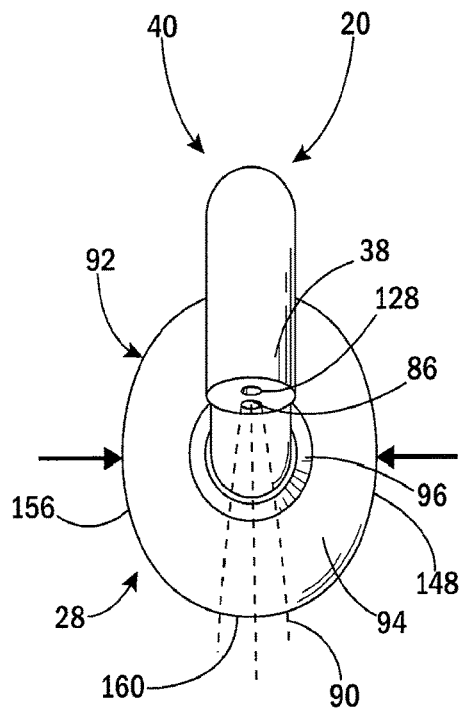
FIG. 8
FIG. 9

HAND HELD IRRIGATION AND SUCTION TOOL

FIELD OF THE INVENTION

The present invention relates to a hand held and hand operated irrigation tool usable during surgery and more particularly to an irrigation tool of hand-held construction that is configured to provide control of irrigation and that is capable of also providing aspiration or suction using the same hand used to control irrigation.

BACKGROUND

Tools for irrigating a wound site or body cavity during surgery are well known in the art. Tools that seek to combine both irrigation and suction have also been attempted in the past. Unfortunately, these have suffered from so many drawbacks that have prevented their commercial success that separate irrigation and suction tools are commonly used today throughout the world during surgery.

One type of irrigation tool commonly used during surgery is referred to as a "turkey baster" or bulb syringe that has a flexible compressible bulb attached to a tube having a nozzle at its free end through which irrigation fluid sucked into the bulb from a pan is discharged from the nozzle when the bulb is squeezed. Unfortunately, use of a bulb syringe to irrigate tissue of a wound site or body cavity during surgery is neither efficient nor expeditious. To draw irrigation fluid into the bulb syringe, the bulb must be compressed by squeezing before the nozzle is placed into the container holding irrigation fluid. After the nozzle is placed into the irrigation fluid container, the bulb is released sucking irrigation fluid through the nozzle, into the tube and into the bulb. Sometimes this process needs to be repeated multiple times, to effectively prime the bulb syringe, in order to charge the bulb syringe with enough irrigation fluid for use. After adequately charging the bulb syringe with irrigation fluid, the bulb syringe must be manipulated with its nozzle directed toward the site of the tissue or body cavity sought to be irrigated. Squeezing the bulb then discharges irrigation fluid from the nozzle onto the tissue or into the body cavity. Once the charge of irrigation fluid in the bulb has been discharged, the whole time consuming process of recharging the bulb syringe with additional irrigation fluid must be undertaken.

One type of aspiration tool or suction tool commonly used to aspirate or suction fluid and debris from tissue and within a body cavity during surgery is known as the Yankauer sucker. The Yankauer sucker has enjoyed widespread commercial success largely because it is inexpensive, simple, lightweight, hand-held, and easy to manipulate during use and operation. The Yankauer sucker is a suction tool with an elongate tube having one end that is hand-held by a user that is attached to a suction line and another end that defines a wand with a nozzle that is manipulated by a user holding the tool so fluid and debris can be sucked into the nozzle and transported through a passage in its tube to the suction line during use and operation.

During surgery, it is common for a surgeon to have to irrigate and aspirate dozens of times. This requires a surgeon to either hold an irrigation tool in one hand and a suction tool in the other hand or requires the surgeon to alternately drop and switch tools as needed, which consumes valuable time either way. While the suction tool can be continuously used to apply suction to aspirate fluid or debris from tissue or from within a body cavity, continuous irrigation fluid flow from a bulb aspirator is simply not possible.

What is needed is an irrigation tool capable of substantially continuous irrigation flow. What is also needed is a combination irrigation and suction tool. What is also needed is a tool of hand-held, simple and economical construction that is capable of providing both irrigation and suction without having to remove the tool from the tissue or body cavity.

SUMMARY OF THE INVENTION

The present invention is directed to a hand-held hand operated irrigation tool for delivering irrigation fluid to a site, such as tissue or a body cavity, during a procedure that can be a surgical, veterinary, or dental procedure that has a handle carrying a manipulable handgrip configured to control the flow of irrigation fluid from the tool in response to manual displacement of the handgrip by a user of the tool grasping and squeezing the handle and handgrip with their hand. In a preferred embodiment, the irrigation tool includes an aspirator integrally formed of the handle operated using the same hand of the user grasping the handle that is used to control irrigation fluid flow.

The irrigation tool has a substantially rigid handle that provides an irrigation fluid conduit and includes a pair of handgrip mounts to which the manipulable handgrip is attached. In a preferred embodiment, the handgrip includes an irrigation flow valve of flow-modulating construction that modulates flow of irrigation fluid from the tool in response to the magnitude of displacement of the handgrip being squeezed by the hand of the user using the tool. The handgrip includes an irrigation fluid reservoir in fluid flow communication with an irrigation fluid conduit defined by a passage leading to a fluid coupling in fluid flow communication with a source of irrigation fluid that preferably is a sterile liquid saline solution. The irrigation fluid reservoir preferably is provided by a compressible chamber mounted to the handle via one of the handgrip mounts that preferably is a fluid coupling that cooperates with the compressible chamber to define an irrigation fluid valve that is normally closed. The compressible chamber includes a flexible sidewall and at least one inlet or outlet defined by a socket that engages the fluid coupling. The fluid coupling includes a tube having an open end defining an open ended valve body that seats against an inner surface of the sidewall adjacent the discharge end of the compressible chamber within the irrigation fluid reservoir of chamber when the valve is closed. When the handgrip is displaced, the sidewall of the compressible chamber deforms causing a valve seat provided by the inner surface of the sidewall against which the open ended valve body seats to be displaced away from the open ended valve body thereby opening the valve. When the handgrip is released or when pressure applied against the handgrip sufficiently reduced, the chamber returns to its original position causing the valve body to re-seat against the compressible chamber sidewall closing the valve. In a preferred valve body embodiment, the open ended valve body is formed of a curved or angled tube, e.g., such as a generally L-shaped tube, having a tube opening that extends generally outwardly towards a longitudinally extending section of the compressible chamber sidewall.

When the valve is opened, irrigation fluid communicated to the irrigation fluid reservoir from the irrigation fluid source is discharged from the compressible chamber through the irrigation fluid conduit and out a port formed in a free end or tip of a wand extending outwardly from the handle.

The valve formed by operable cooperation between the compressible chamber and the fluid coupling preferably is a flow-modulating control valve responsive to the amount of displacement of the handgrip when the handle is grasped by a hand of a user of the tool and squeezed causing the handgrip to displace. In a preferred embodiment, the hand of a user of the tool directly engages at least a portion of the sidewall of the compressible chamber opening the valve when the handgrip is squeezed deforming at least part of the compressible chamber sidewall. When released or when pressure applied to the compressible chamber sidewall is sufficiently reduced, the compressible chamber returns to its original shape closing the valve stopping irrigation fluid flow.

In a preferred embodiment the compressible chamber is provided by a bulb that preferably is a squeeze bulb of elastomeric construction having an inlet or first fluid coupling engaging socket at one end and an outlet or second fluid coupling engaging socket at its opposite end. The squeeze bulb is mounted to the fluid couplings in a longitudinal direction extending along the hand rest so that at least one side of the bulb is supported by the hand rest when squeezed during use and operation of the tool. When squeezed, at least part of a sidewall of the bulb is deformed compressing the bulb, opening the valve, and forcing irrigation fluid from the bulb out the tool. When released, the bulb returns to its original shape closing the valve and blocking irrigation fluid flow.

In a preferred embodiment, each handgrip mount includes a fluid coupling that is coupled to the compressible chamber with one of the fluid couplings cooperating with the compressible chamber to form an irrigation fluid flow-modulating control valve that is configured to vary the rate of flow of irrigation fluid discharge from the tool in response to the magnitude and/or rate of squeezing pressure or force applied by a hand grasping the handle squeezing the compressible chamber. Such a flow-modulating valve configuration advantageously allows the flow rate of irrigation fluid discharge from the tool to be varied from as little as a drop or two a minute to as much as 60 cubic centimeters (cc's) per ten seconds, i.e., 360 cc's per minute, by varying the amount of squeezing pressure applied to the compressible chamber by the hand of a person grasping the handle and squeezing the handgrip.

The handle also includes a generally longitudinally extending hand rest of substantially rigid construction against which part of the compressible chamber can be supported, enabling a hand grasping the handle to obtain leverage by engaging the hand rest and squeezing the handgrip urging part of the chamber against part of the hand rest compressing at least part of the chamber. Where the tool is configured to provide suction or aspiration, the hand rest includes a longitudinally extending suction conduit in fluid flow communication with a suction control valve that can regulate suction flow that is hand operable using the same hand grasping the handle that is used to control irrigation fluid flow.

The handle and handgrip are configured to enable a user to grasp the handle of the tool with their hand in a plurality of grip configurations including a forehand grip where their palm overlies the hand rest with their thumb engaging part of the flexible chamber sidewall at a location spaced from the location where the open ended valve body seats and one or more fingers engaging another part of the flexible chamber sidewall at another location spaced from the location where the open ended valve body seats, a pencil type grip where their palm generally underlies or is disposed alongside the hand rest with their thumb engaging part of the flexible chamber sidewall at a location spaced from where the open ended valve body seats and one or more fingers engaging another part of the flexible chamber sidewall at another location spaced from where the open ended valve body seats, and a golf grip where their thumb overlies the hand rest and the palm and part of the fingers wrap around the exterior of the flexible chamber sidewall. One or more of these grips enable the handle to be grasped by a hand of a user and the compressible chamber pinched between the thumb and index finger or ring finger in a manner that enables precise control of irrigation fluid flow. The handle and handgrip advantageously produces a tool that is controlled using one hand that not only controls and regulates irrigation fluid flow discharge from the tool but which also controls suction using the same hand grasping the handle.

Various other features, advantages and objects of the present invention will be made apparent from the following detailed description and the drawings.

BRIEF DESCRIPTION OF THE DRAWINGS

One or more preferred exemplary embodiments of the invention are illustrated in the accompanying drawings in which like reference numerals represent like parts throughout and in which:

FIG. 2 is a top plan view of the tool of FIG. 1 illustrating a handgrip of the tool in an un-displaced state;

FIG. 3 is a front elevation view of the tool of FIG. 1 illustrating the handgrip of the tool in an un-displaced state;

FIG. 8 is a top plan view of the tool illustrating the handgrip displaced from being squeezed by the hand (not shown) of a user squeezing the handgrip discharging liquid irrigation fluid;

FIG. 9 is a front elevation view of the tool illustrating the handgrip displaced from being squeezed by the hand (not shown) of a user causing liquid irrigation fluid to be discharged;

Figure 1:
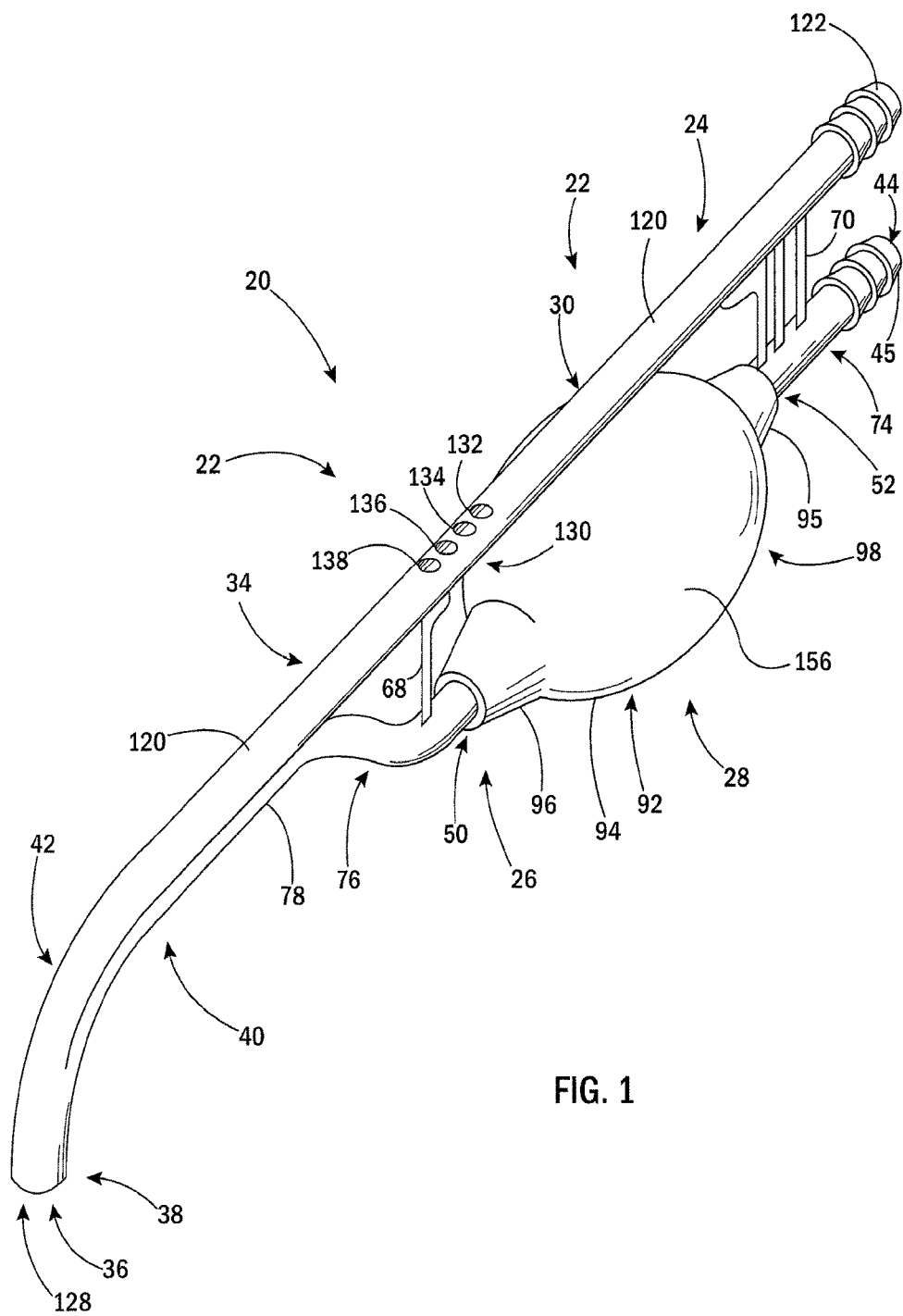
FIG. 1 is a perspective view of an irrigation tool according to the present invention.

Before explaining one or more embodiments of the invention in detail, it is to be understood that the invention is not limited in its application to the details of construction and the arrangement of the components set forth in the following description as well as illustrated in the drawings. The invention is capable of other embodiments, which can be practiced or carried out in various ways. Also, it is to be understood that the phraseology and terminology employed herein is for the purpose of description and should not be regarded as limiting

DETAILED DESCRIPTION

Figure 4:
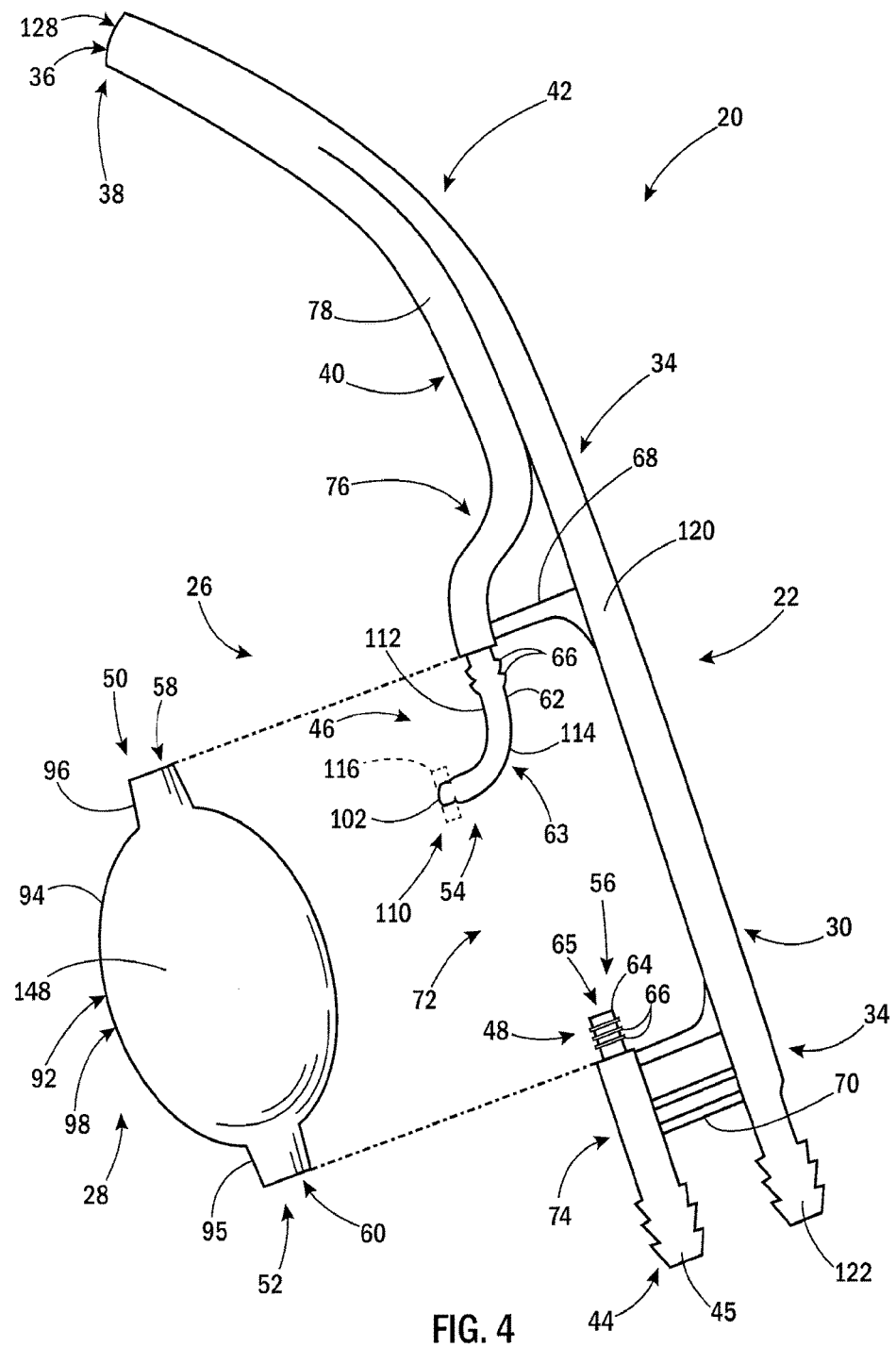
FIG. 4 is a perspective exploded view of the tool.
Figure 5:
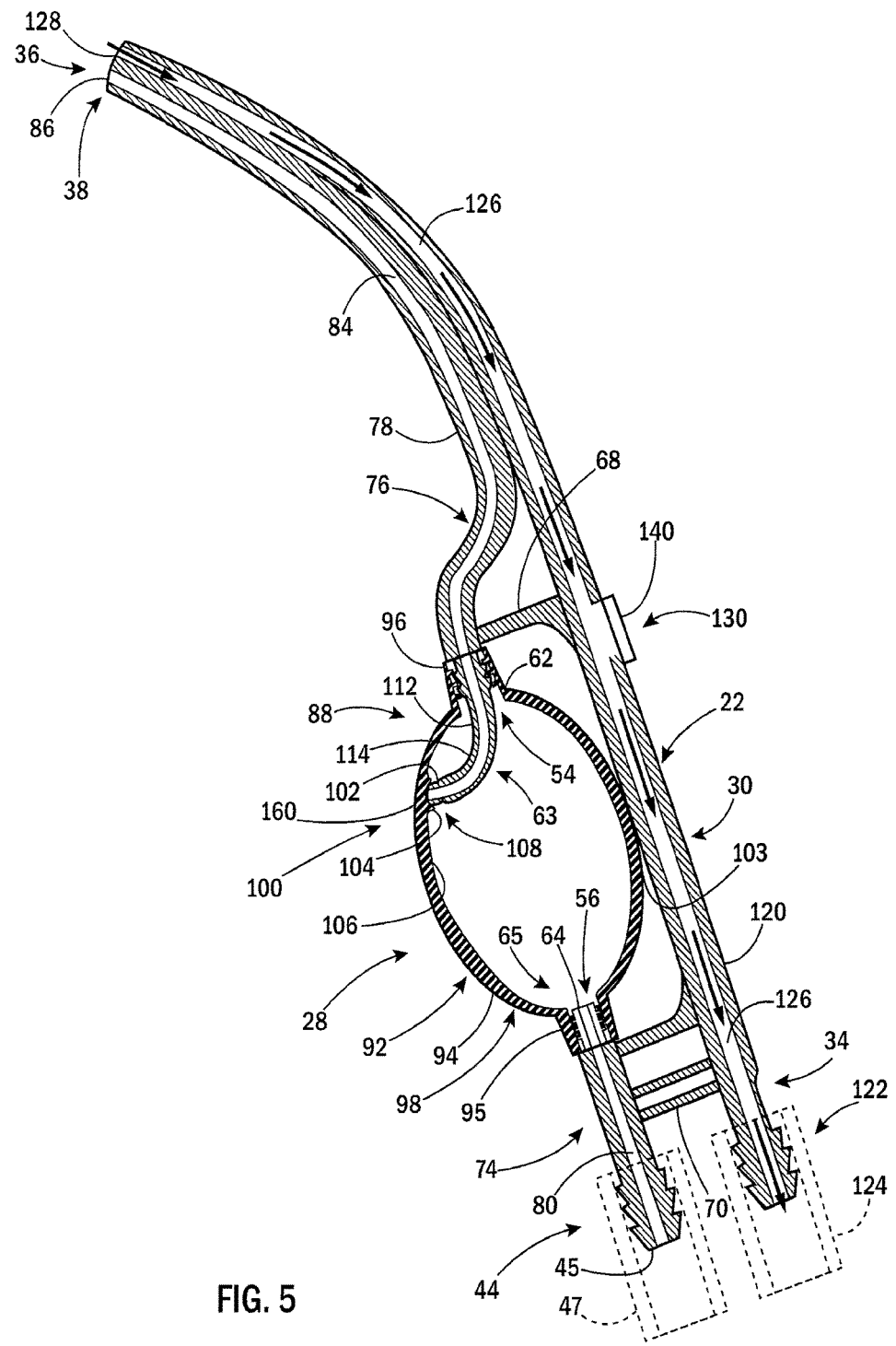
FIG. 5 is a cross-sectional view of the assembled tool with the handgrip in an un-displaced state.
Figure 6:
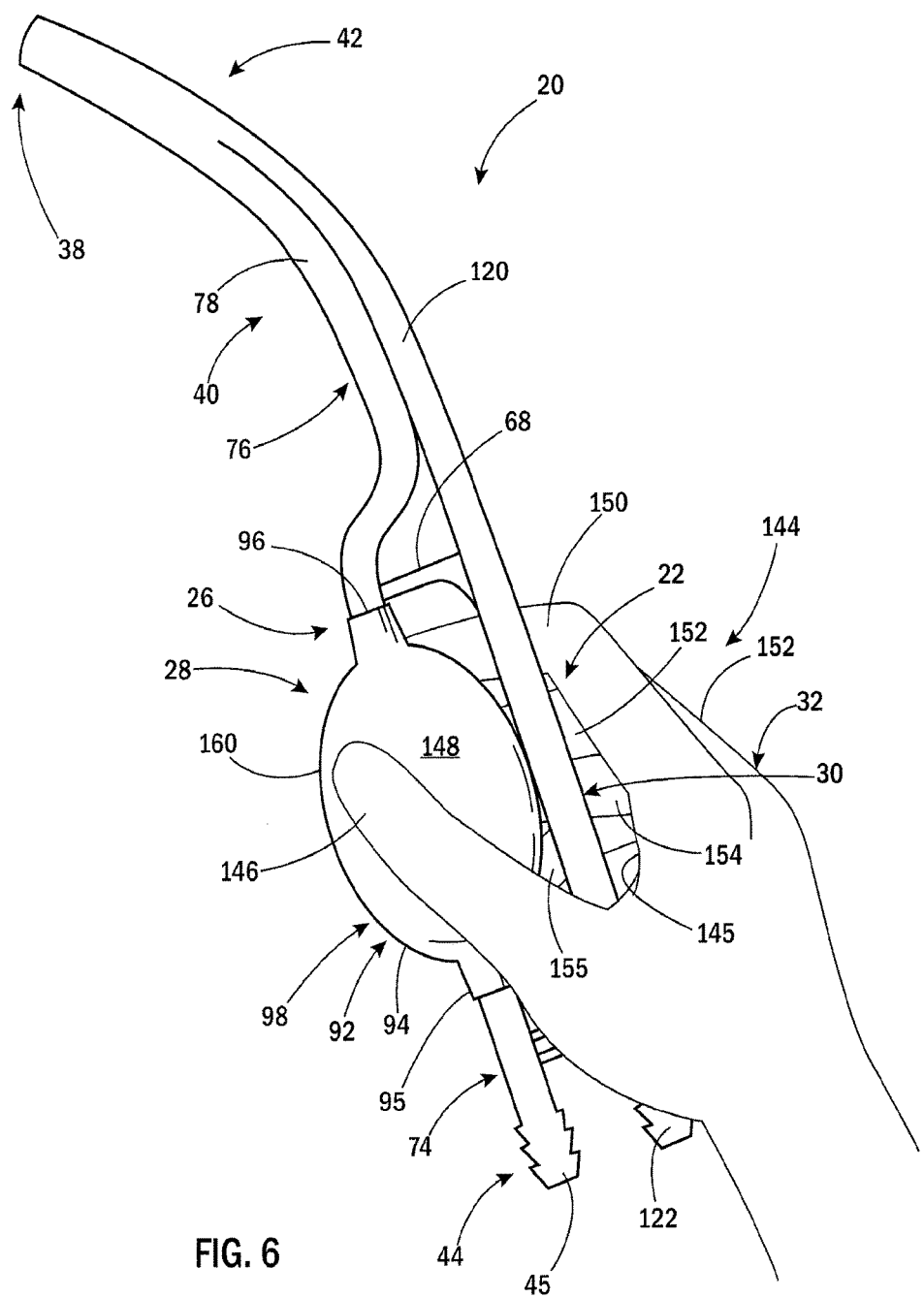
FIG. 6 is a perspective view of the tool illustrating a handle of the tool being grasped by a hand of a user with the handgrip in an un-displaced state.
Figure 7:
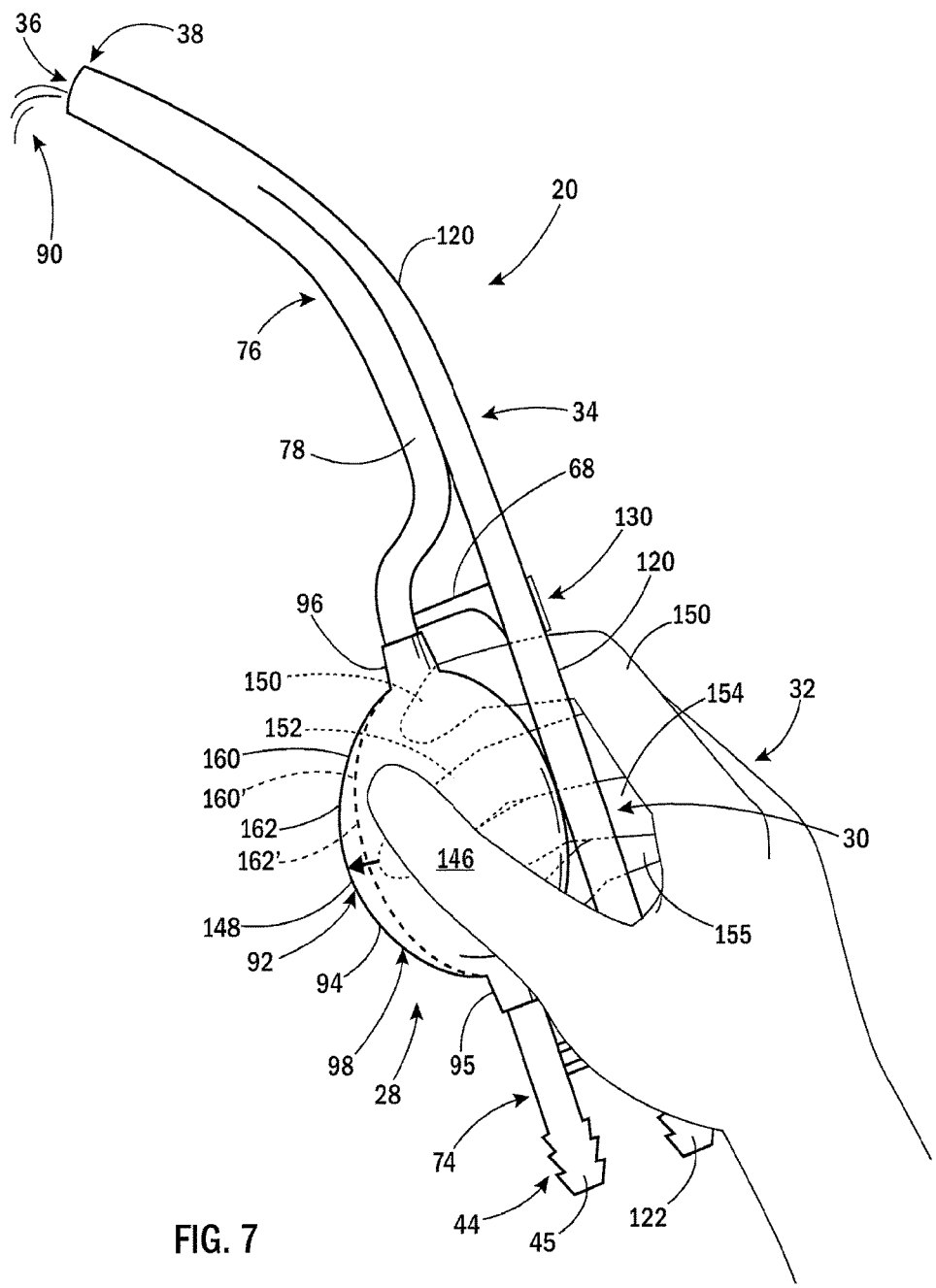
FIG. 7 is a perspective view of the tool grasped by a hand of a user applying squeezing pressure to the handgrip displacing the handgrip by deforming or compressing the handgrip causing irrigation fluid to be discharged from the tool.

FIGS. 1-10 illustrate a preferred embodiment of an irrigation tool 20 suitable for use in surgical, veterinary, and dental applications that is of hand-held construction and configured to provide touch-responsive irrigation fluid flow modulation during use enabling selective one-handed control of flow of irrigation fluid from the tool 20 to be varied from a drop at a time, to a dribble, and all the way to a stream depending on the need of the user. The tool 20 includes a handle 22 that serves as a substantially rigid frame 24 that includes a mount 26 that holds an irrigation fluid flow-controlling displaceable handgrip 28. The handle 22 includes a hand rest 30 extending alongside the handgrip 28 that supports part of a hand 32 of a user holding the tool 20 enabling engagement of the handgrip 28, such as depicted in FIGS. 6 and 7, in a manner where the user can selectively control the amount of irrigation fluid flow from the tool 20 as well as prevent any irrigation fluid from being discharged from the tool 20. The hand rest 30 not only serves as a structural backbone or spine that provides support to the handgrip 28, the hand rest 30 provides leverage to a hand 32 grasping the handle 22 and squeezing the handgrip 28 as depicted in FIG. 7. Depending on the type of hand grip employed by a user of the tool 20, the hand rest 30 can also help provide handgrip squeezing leverage to a hand 32 grasping both the hand rest 30 and the handgrip 28 at the same time, such as depicted in FIGS. 6 and 7. Such a tool 20 constructed in accordance with the present invention can be used a stand-alone irrigator, but is also particularly well suited for being configured with an aspirator 34 whose operation is controlled using the same hand 32 grasping the handle 22 that controls flow of irrigation fluid, as discussed in more detail below.

The tool 20 includes an irrigation fluid discharge 36 disposed at a free end or tip 38 of a wand 40 extending outwardly from the handle 22. If desired, the wand 40 can be shaped or otherwise configured for ease of use including facilitating irrigation fluid delivery into a body cavity or the like during operation. For example, the wand 40 shown in FIGS. 1-10 can be configured with a curved section 42 disposed at or adjacent its free end 38 that angles the irrigation fluid discharge 36 generally downwardly when the tool 20 is grasped by a hand 32 of a user in the manner depicted in FIGS. 6 and 7. The tool 20 also includes an irrigation fluid intake 44 carried by the handle 22 disposed at an end of the tool 20 opposite that of the irrigation fluid discharge 36. During operation, irrigation fluid from a source of irrigation fluid delivered to the intake 44 is conveyed through the tool 20 and expelled from the discharge 36 when pressure is manually applied to the handgrip 28 by a user grasping the handle 22 and squeezing the handgrip 28. In a preferred embodiment, a liquid irrigation fluid source, such as a plastic IV bag containing sterile saline solution, is connected to a barbed fluid coupling 45 of the irrigation fluid intake 44 by a tube 47, shown in phantom in FIG. 5, of an IV line that is in turn connected to a 500 or 1000 milliliter bag (not shown) of sterile saline solution hung on a vertically extending hanger at a sufficient height to substantially continuously gravity feed liquid irrigation fluid to the tool 20 during use and operation. In a preferred embodiment, the plastic IV bag of sterile saline solution is hung on a hanger so it is at a height above the tool 20 and can be a couple of feet higher than the tool 20 to provide sufficient head or pressure when being continuously gravity fed from the bag to the tool 20. In a preferred embodiment, the plastic IV bag of sterile saline solution is hung at a height higher than waist level, e.g., higher than three feet above the ground, and preferably hung at a height at least a couple of feet above waist level. As is discussed in more detail below, the rate of flow of irrigation fluid expelled out the discharge 36 of the tool 20 during use is variable and dependent on selective application of pressure to the handgrip 28 during squeezing of the handgrip 28.

With reference to FIGS. 4 and 5, the handgrip mount 26 is integrally formed of the hand rest 30 and includes a pair of spaced apart handgrip mounting seats 46 and 48 carried by the hand rest 30 that engage and help hold the handgrip 28 in place when attached to the handle 22. The handgrip mounting seats 46 and 48 are configured to engage generally complementarily configured opposed mounting seats 50 and 52 of the handgrip 28 during attachment of the handgrip 28 to the handle 22. Engagement can be releasable so as to enable removal and re-attachment of the handgrip 28 to the handle 22 if desired.

In a preferred embodiment, at least one of the mounting seats 46 or 48 of the handgrip mount 26 includes either an anchor or a socket and at least one of the mounting seats 50 and 52 of the handgrip 28 includes either an anchor or a socket. With reference to FIGS. 4 and 5, each mounting seat 46 and 48 of the handgrip mount 26 includes a corresponding outwardly extending anchor 54 and 56 and each mounting seat 50 and 52 of the handgrip 28 includes a socket 58 and 60 that receives a corresponding one of the anchors 54 and 56. If desired, the handgrip 28 can be configured so that at least one of its sockets, such as socket 60, is an anchor that extends outwardly from the handgrip 28, and the handgrip mount 26 configured so that at least one of its anchors, such as anchor 56, is instead configured as a socket.

As is best shown in FIGS. 4 and 5, each anchor 54 and 56 is a nipple 62 and 64 having barbs or ridges 66 that frictionally engage the interior of a corresponding socket 58 and 60 formed in the handgrip 28 when the handgrip 28 is attached to the handle 22. The nipples 62 and 64 can be carried by arms 68 and 70 extending from the hand rest 30 that space the nipples 62 and 64 and orient them so they oppose one another defining a handgrip receiving receptacle 72 therebetween in which the handgrip 28 having oppositely disposed sockets 58 and 60 is received when attached to the handle 22. When the handgrip 28 is attached to the handle 22, the discharge end nipple 62 is received in the discharge end socket 58 of the handgrip 28 and the inlet end nipple 64 is received in the inlet end socket 60 of the handgrip 28. If desired, each arm 68 and 70 can be an integrally formed portion or section of the hand rest 30.

The hand rest 30 carries spaced apart sections 74 and 76 of an irrigation fluid conduit 78 that is in fluid flow communication with the handgrip 28 when the handgrip 28 is attached to the handle 22. As is best shown in FIGS. 3 and 4, a corresponding irrigation fluid conduit section 74 and 76 extends from a respective one of the arms 68 and 70. The irrigation fluid conduit section 74 upstream of the handgrip 28 includes a fluid conveying passage 80 that extends from the irrigation fluid intake 44 to an adjacent handgrip mounting anchor 56 so the passage 80 is in fluid flow communication with an irrigation fluid reservoir 82 within the handgrip 28. The conduit section 76 downstream of the handgrip 28 includes a fluid conveying passage 84 that extends from adjacent handgrip mounting anchor 54 to a discharge port 86 at the tip 38 of the wand 40 enabling irrigation fluid to be conveyed from the reservoir 82 to the discharge 36 during operation.

The nipples 62 and 64 that form corresponding handgrip anchors 54 and 56 respectively provide fluid couplings 63 and 65 that not only mount the handgrip 28 to the handle 22, but which also enable irrigation fluid to be conveyed to and from the handgrip 28. Such a fluid coupling handgrip mounting arrangement 88 is advantageous in that it is of simple construction using mounting anchor nipples 62 and 64 of fluid couplings 63 and 65 through which irrigation fluid passages 80 and 84 extend to mount the handgrip 28 to the handle 22 that also convey irrigation fluid to and from the handgrip 28.

Figure 10:
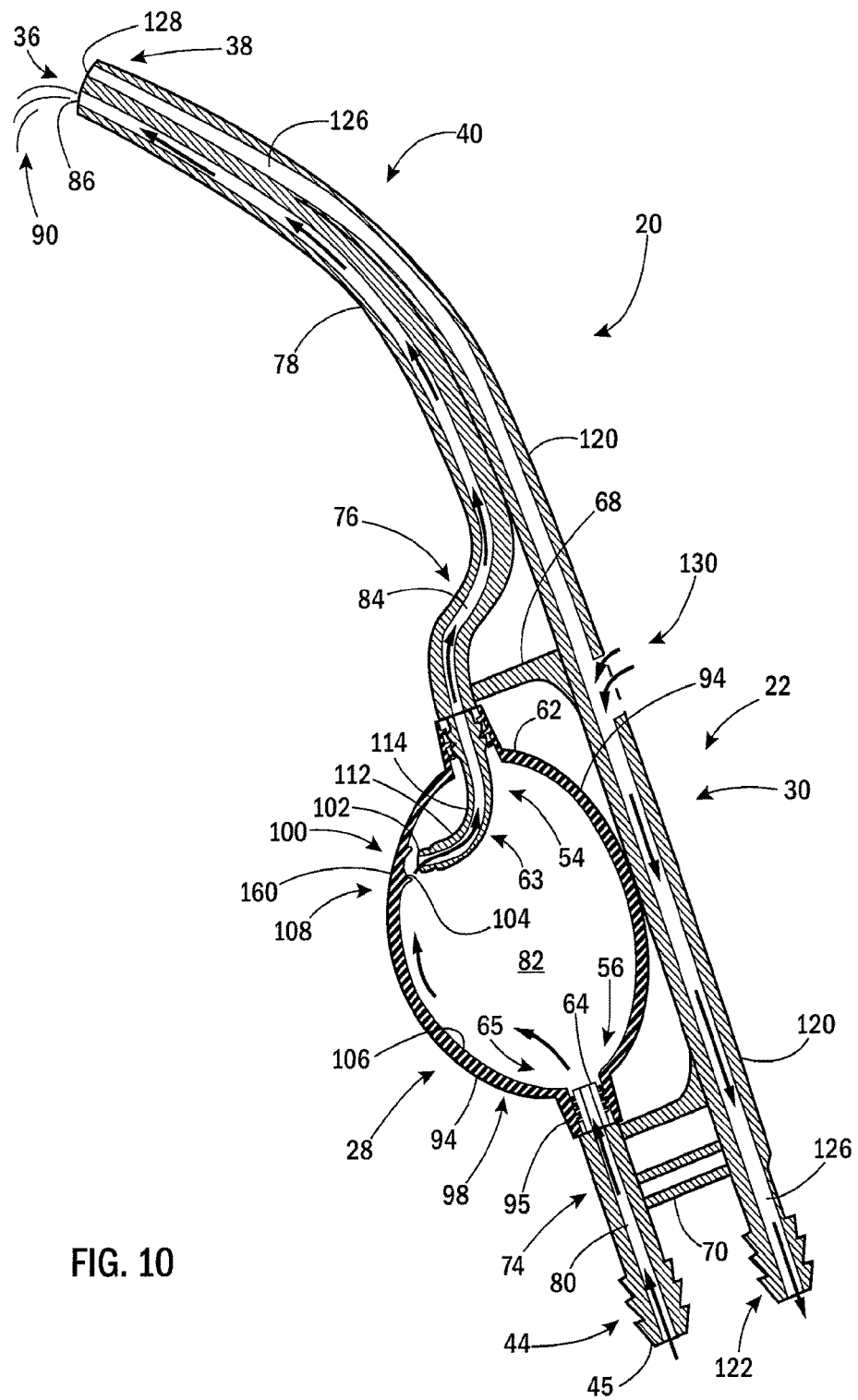
FIG. 10 is a cross-sectional view of the tool with the handgrip displaced from being squeezed by the hand (not shown) of a user causing liquid irrigation fluid to be discharged.

During operation, the upstream passage 80 conveys irrigation fluid 90 from an irrigation fluid source, such as a source of liquid that can be a sterile solution, e.g., sterile saline solution, to the reservoir 82 within the handgrip 28 charging the reservoir 82 with fluid. When the handgrip 28 is displaced, preferably by being manually squeezed, irrigation fluid flows from the reservoir 82 through the downstream passage 84 and out the discharge port 86 as depicted in FIGS. 8-10.

The irrigation fluid reservoir 82 is provided by a compressible irrigation fluid holding chamber 92 having a sidewall 94 that can be of tubular and endless construction and that is at least partially flexible in response to a squeezing force applied to the handgrip 28. The sidewall 94 of the irrigation fluid holding chamber 92 extends between an inlet 95 at one end and an outlet 96 at an opposite end that can be formed to respectively include or otherwise provide a corresponding one of the mounting sockets 58 and 60. As previously discussed, socket 58 corresponds to an outlet of the compressible chamber 92 and socket 60 corresponds to an inlet of the chamber 92.

In a preferred embodiment, the compressible chamber 92 is tubular and provided by a squeeze bulb 98 that can be of oval or oblong construction, can be elongate, and can be of elastomeric construction. In one preferred embodiment, the squeeze bulb 98 is made of an elastomeric material, such as a rubber, e.g. silicone rubber, having its inlet socket 60 opposite its outlet socket 58 and preferably generally in-line, e.g., generally coaxial, therewith. While the handgrip 28 is provided by the squeeze bulb 98 in the preferred embodiment of the tool 20 shown in FIGS. 1-10, it should be recognized that the handgrip 28 can include other components, not shown, in addition to the squeeze bulb 98, including components which can cooperate with, e.g., engage or otherwise contact, the squeeze bulb 98 during use and operation.

With reference to FIGS. 4-10, the displaceable handgrip 28 cooperates with one of the fluid couplings, preferably the outlet end fluid coupling 63, to form an irrigation fluid flow-modulating control valve arrangement 100 that not only enables irrigation fluid flow to flow from the irrigation reservoir when the handgrip 28 is displaced but which also enables selective control of the rate of flow discharged from the tool 20 responsive to one or more of the rate and magnitude of displacement of the handgrip 28 and/or one or more of the rate and magnitude of force applied to the handgrip 28 to displace the handgrip 28. In a preferred embodiment, such a flow-modulating control valve arrangement 100 constructed in accordance with the present invention enables the flow rate of liquid irrigation fluid discharged from the tool 20 to be relatively precisely controlled and varied in response to a lesser or greater amount of squeezing pressure manually applied by a hand 32 squeezing the handgrip 28 during use and operation of the tool 20 enabling the flow rate discharged from the tool 20 to be varied from as little as a single cubic centimeter per minute to surge flow of as much as three hundred and sixty cubic centimeters per minute. Such a flow-modulating valve arrangement 100 constructed in accordance with the present invention also enables the flow rate of liquid irrigation fluid discharged from the tool 20 to be controlled and varied in response to the rate of change of squeezing pressure manually applied by a hand 32 squeezing the handgrip 28. Such an irrigation tool 20 constructed in accordance with the present invention is hand held and hand controlled enabling the tool 20 to dispense just a drop or two of irrigation fluid at a time when and where needed whose flow can be increased even in short bursts or surges to forcefully discharge enough irrigation fluid flow to break loose coagulated blood from tissue without the need to resort to trauma-inducing surgical instruments to do so. Such an irrigation tool constructed in accordance with the present invention is advantageously capable of substantially continuous use because bags of sterile saline solution can be changed quickly and easily during use without interrupting flow in many cases.

The fluid coupling 63, which is in fluid flow communication with irrigation fluid passage 84, is elongate and has a tubular open-ended valve body 102 seated against a valve seat 104 of a longitudinally extending interior surface 106 of the flexible compressible chamber sidewall 94 forming a normally closed valve 108 that is closed when seated as shown in FIG. 5. The valve 108 remains seated when no squeezing pressure is applied to the handgrip 28 or a minimal amount of squeezing pressure is applied that is insufficient to deform or otherwise displace the valve seat 104 of the chamber sidewall 94 away from the valve body 102. When another part of the chamber sidewall 94 spaced from the valve seat 104 is displaced, such as during squeezing of the handgrip 28, it causes the valve seat 104 to move away from the open-ended valve body 102 of the fluid coupling 63 unseating the valve body 102, such as depicted in FIG. 10, enabling irrigation fluid from the compressible chamber 92 to flow through the downstream passage 84 and out the discharge port 36. As is best shown in FIGS. 5 and 10, the open-ended valve body 102 is a tube 112 having its open end seating against the seat 104 when closed and unseating from the seat 104 when opened when the compressible chamber 92 is squeezed. When released or squeezing pressure sufficiently reduced, the compressible chamber 92 returns substantially to its original shape causing the valve seat 104 to re-seat against the open-ended valve body 102 stopping irrigation fluid from being discharged from the tool 20.

Such a valve 108 is of flow-modulating construction because the rate of flow of irrigation fluid discharged from the compressible chamber 92 though the unseated open-ended valve body 102 increases with increasing space from the valve seat 104 which in turn increases with increasing squeezing pressure applied to the compressible chamber sidewall 94 by a hand 32 of a user squeezing the handgrip 28 during use. The flow-modulating valve 108 also modulates flow in response to the rate of application of squeezing pressure to the handgrip 28 because the rate of irrigation fluid flow discharged from the tool 20 increases as the rate that squeezing pressure is applied to the handgrip 28 increases. This feature advantageously enables a user of the tool 20 to initiate a surge in irrigation fluid flow discharged from the tool 20 by rapidly manually squeezing the handgrip 28 with enough force.

The open-ended valve body 102 is formed by a tubular portion 110 (FIG. 4) of fluid coupling 63 that is oriented to dispose the valve body 102 so it seats against a longitudinally extending portion of the chamber sidewall 94 that defines the seat 104 against which the valve body 102 seats when the valve 108 is closed. In the preferred embodiment shown in FIGS. 4, 5 and 10, the tubular portion 110 is an angled or curved tube 112 having a bend 114 that can be generally L-shaped that orients the open-ended valve body 102 so its open end faces generally radially outwardly toward the seat 104 of the chamber sidewall 94. In the preferred embodiment of the compressible chamber 92 shown in FIGS. 5 and 10, seat 104 can be of a recessed or concave configuration, such as the rounded dimple best shown in FIG. 10, integrally formed, e.g., molded, in the interior surface of the chamber sidewall 94. If desired, the seat 104 can be formed of a substantially smooth portion of the interior surface of the chamber sidewall 94, such as the portions of the interior surface 106 of the chamber sidewall shown in FIGS. 5 and 10 on either side of the seating portion 104. If desired, the open-ended valve body 102 can include or carry a seal 116 (shown in phantom in FIG. 4) that can be of annular construction to help facilitate seating when the valve 108 is closed. Where such a seal 116 is used, the seal can be annular and formed of an elastomeric material, such as a rubber, e.g., silicone rubber, that is attached to the valve body 102 at or adjacent its free end, such as depicted in phantom in FIG. 4.

As previously discussed, a tool 20 constructed in accordance with the present invention is particularly well suited to be configured to include an aspirator 34 of integral construction. The aspirator 34 is integrally formed of part of the handle 22 of the tool 20 having a suction conduit 120 integrally formed of the hand rest 30 and wand 40. As is best shown in FIG. 5, the suction conduit 120 has a barbed suction coupling 122 connected to a vacuum or suction line 124 (shown in phantom in FIG. 5) that is in turn connected to a source of suction or vacuum that communicates the suction through an elongate fluid conveying suction passage 126 integrally formed in the suction conduit 120 during operation. The suction passage 126 extends to a suction intake port 128 disposed in the tip 38 of the wand 40 that is located adjacent the irrigation fluid discharge port 86.

Where the tool 20 is configured with an aspirator 34, the handle 22 preferably includes a suction flow regulating valve 130, e.g., suction control vent, whose operation is controlled using the same hand 32 grasping the handle 22 that is used to control flow of irrigation fluid producing a tool 20 that advantageously provides one-handed operation and control of both irrigation and suction. As is shown in FIGS. 1 and 2, the suction flow regulating valve 130 can include a plurality of suction vents 132, 134, 136 and 138 that communicate with the atmosphere or ambient when open to selectively divert some or all of the suction away from the tip 38 of the tool 20 depending on the number of vents 132, 134, 136 and 138 left open depending on the amount of suction desired. Where no suction is desired at the tip 38, all of the suction vents 132, 134, 136 and 138 are left open or unobstructed. Depending on the amount of suction desired at the tip 38, one or more of the suction vents 132, 134, 136 and 138 are closed using one or more of the digits of the hand 32 grasping the handle 22 to block or seal them. Where maximum suction at the tip 38 is desired, the suction flow regulating valve 130 can be closed, such as by manually blocking all of the suction vents 132, 134, 136 and 138 at the same time using the same hand 32 grasping the handle 22 that is used to control irrigation fluid flow.

If desired, a suction vent or valve actuator 140 can be provided, such as is shown in FIG. 5, that blocks or seals all of the suction vents 132, 134, 136 and 138 can be displaceable, e.g., slidable, or even removable. If desired, the suction vent or valve actuator 140 can be a removable plug, such as a plug made of an elastomeric material, e.g., silicone rubber, which can remain in place where constant suction at the tip 38 is desired or where the tool 20 is not going to be connected to a source of suction. Where it is desired to use the suction flow regulating valve 130, the suction control valve actuator 140, e.g., plug, can be removed. If desired, the suction control valve actuator 140 can be a slide or have a different configuration or construction.

The handle 22 is of one-piece, unitary and substantially homogenous construction preferably molded of a plastic, such as acrylonitrile butadiene styrene (ABS), cellulose acetate, cellulose acetate butyrate, polystyrene, polycarbonate, polystyrene, polypropylene, or another suitable plastic. Such a handle 22 formed of plastic is advantageously lightweight, substantially rigid permitting tissue penetration during use, durable, economical and can be of disposable construction. If desired, the handle 2 can be formed of a metal, such as a stainless steel suitable for surgical and/or dental use, such as where re-use of the tool 20 is desired.

The handle 22 is integrally formed with a hand rest 30 that includes an integrally formed suction conduit 120 with the suction passage 126 extending within the conduit 120 substantially the length of the tool 20 including into the wand 40 to the tip 38. As is shown in the drawing figures, the suction conduit 120 and the irrigation fluid conduit 74 converge at the wand 40. The handle 22 is also integrally formed to include the handgrip receiving receptacle 72 having a pair of fluid couplings 63 and 65 integrally formed of the handle 22 that fluid-tightly capture the compressible chamber 92 of the handgrip 28 when attached to the handle 22 during assembly. The handle 22 is further integrally formed to include an irrigation fluid conduit 78 that extends alongside the integrally formed suction conduit 120 that extends substantially the length of the tool 20 to the tip 38 of the wand 40. As is shown in FIGS. 1-10, the irrigation fluid conduit 78 and suction conduit 120 can extend substantially parallel to one another along at least part of the length of the tool 20 including along the wand 40 as well as along the opposite end of the tool 20 where the conduits 78 and 120 respectively connect to irrigation and suction lines 47 and 124 (FIG. 5). In the preferred tool embodiment shown in the drawings, the suction conduit 120 and irrigation fluid conduit 78 are arranged in an over-under configuration where the suction conduit 120 overlies the irrigation fluid conduit 78. As is also shown in the drawings, the portion of the suction conduit 120 formed of the hand rest 30 of the handle 22 generally lies alongside and overlying the compressible chamber 92 when the tool 20 is generally oriented in its operating position shown in FIGS. 1, 6 and 7.

The integrally formed irrigation fluid conduit 78 includes an irrigation fluid conduit section 76 disposed downstream of the compressible chamber 92 that also includes the integrally formed fluid coupling 63 that is not only used to mount the compressible chamber 92 to the handle 22 but which also cooperates with the compressible chamber 92 in forming the flow-modulating valve arrangement 100. Integrally formed fluid coupling 63 also includes an integrally formed open-ended valve body 102 in fluid flow communication with the downstream conduit section 76 that seats against part of the interior surface 106 of the compressible chamber 92 when the chamber 92 is mounted to the handle 22 defining the normally closed flow-modulating valve 108.

The irrigation fluid conduit 78 also includes an irrigation fluid conduit section 74 disposed upstream of the compressible chamber 92 that also includes the integrally formed fluid coupling 65 that is used to mount the compressible chamber 92 to the handle 22 together with fluid coupling 63. The irrigation fluid conduit section 74 also includes an integrally formed irrigation line coupling 44 opposite fluid couplings 63.

In the preferred embodiment of the tool 20 shown in FIGS. 1-10, the compressible chamber 92 is an oval or oblong hollow squeeze bulb 98 having sockets 58 and 60 at opposite ends of the bulb 98 that fluid tightly receive a corresponding fluid coupling 63 and 65 used to mount the bulb 98 to the handle 22 while providing fluid tight frictional engagement therebetween. During assembly, the end of the squeeze bulb 98 having socket 58 is telescoped over the hook shaped fluid coupling 63 by manipulating the bulb 98 so the open-ended valve body 102 enters the socket 58. The bulb 98 is manipulated so the open-ended valve body 102 is urged interiorly of the bulb 98 into the irrigation fluid reservoir 82 within the bulb 98 along with the bend 114 of the tube 112 of the portion of the fluid coupling 63 until the valve body 102 seats against the sidewall 94 of the bulb 98 forming the flow-modulating valve arrangement 100. When the valve body 102 is seated against the sidewall 94 of the bulb 98, the barbs 66 of the nipple 62 portion of the fluid coupling 63 are received in the socket 58 of the bulb 98 providing fluid tight frictional engagement with the bulb 98. The bulb 98 is further manipulated so that the opposite nipple 64 of the other fluid coupling 65 is inserted into the opposite socket 60 at the other end of the bulb 98 until the barbs 66 of the nipple 64 frictionally engage the bulb 98 providing fluid tight frictional engagement therebetween. When the bulb 98 is mounted to the handle 22, a portion 103 of the bulb sidewall 94 can abut or bear against part of the substantially rigid hand rest 30 as shown in FIG. 5 such that the hand rest 30 acts as a substantially rigid spine or backbone that supports the bulb 98 helping to enable it to be compressed when squeezed. In a preferred embodiment, the engagement provided between each fluid coupling 63 and 65 of the handle 22 and the corresponding socket 58 and 60 of the bulb 98 is a snap fit engagement facilitating quick and easy attachment of the bulb 98 to the handle 22 as well as quick and easy removal of the bulb 98 from the handle 22 in instances where bulb removal is desired.

In use and operation, the irrigation fluid coupling 45 of the tool 22 is attached to a line connected to a source of liquid irrigation fluid that preferably is a bag of saline solution hung sufficiently high above the floor so that irrigation fluid flow provided to the irrigation fluid reservoir 82 in the squeeze bulb 98 is substantially continuous enabling substantially continuous replenishment of irrigation fluid discharged from the reservoir 82 when the bulb 98 is squeezed by a hand 32 of a user grasping the handle 22 and squeezing the bulb 98. The suction line coupling 122 is attached to a line connected to a source of a vacuum, such as a vacuum pump or the like.

With specific reference to FIGS. 6 and 7, the construction of the handle 22 of the tool 20 is advantageous in that it allows a user to grasp the handle 22 of the tool 20 with one hand 32 and control both the irrigation fluid and suction functions of the tool 20 using one hand 32 substantially at the same time. As is described in more detail below, the construction of the handle 22 of the tool 20 is also advantageous in that it allows a user to grasp the handle 22 with one hand 32 using a plurality of types of grips.

For example, as is shown in FIGS. 6 and 7, the hand 32 of the user is grasping the handle 22 using a knife-holding or forehand grip 144 where part of the palm 145 of the hand 32 overlies part of the hand rest 30 positioning a thumb 146 of the hand 32 so it bears against one side 148 of the bulb sidewall 94 and a plurality of fingers 150, 152, 154 and 155 so at least one of the fingers, such as the index finger 150, the ring finger 152, the middle finger 154 or the little finger 155, bears against an opposite side 156 enabling a squeezing pressure to be applied by the hand 32 against one or both sides 148 and 156 of the sidewall 94 on either side of the valve 108 of the squeeze bulb 98 to open the valve 108 by unseating the open-ended valve body 102 from the interior surface 106 of the sidewall 94 of the squeeze bulb 98 allowing irrigation fluid that has collected in the reservoir 82 to flow out the bulb 98. In a preferred method of operation, squeezing pressure is applied to both sides 148 and 156 of the bulb 98 displacing the handgrip 22 causing the seat 104 of the bulb 98 to displace outwardly away from the valve body 100, such as depicted by FIGS. 7-10, opening the valve 108 allowing irrigation fluid in the reservoir 82 to flow out of the bulb 98 and be discharged from the tool 20. When released, the seat 104 of the bulb 98 returns to its original position seating against the valve body 100 closing the valve 108.

With specific reference to FIGS. 7 and 10, as squeezing pressure is applied to one or both sides 148 and 156 of the bulb 98, an outer portion 160' of the bulb sidewall 94 located opposite the valve seat 104 is displaced outwardly from the position 162' shown in phantom in FIG. 7 away from the valve body 102 to the position 162 shown in solid in FIG. 7. For example, as the thumb and one or more fingers of the hand 32 grasping the handle 22 are pinched together, the outer portion 160 of the bulb sidewall 94 overlying the valve body 102 displaces outwardly away from the valve body 102 opening the valve 108 allowing irrigation fluid to be discharged out the tip 38 of the tool 20. For example, the bulb 98 can be pinched between the thumb 146 and the index finger 150, middle finger 152 and/or the ring finger 154 such as depicted in FIG. 6 enabling relatively precise control or regulation of irrigation fluid flow to be achieved because squeezing pressure can be precisely regulated or controlled by manually pinching the bulb 98 in such a manner.

Advantageously, fingertip pressure can be applied to one or both sides 148 and 156 of the bulb 98 on either side of the valve 108 as needed to modulate irrigation fluid flow out the tip 38 of the tool 20 in a manner that very minimally unseats the sidewall 94 from the valve body 102 permitting control of flow so that only a drop or two is discharged from the tip 38 of the tool 20. Visual feedback can be employed by a user watching how much irrigation fluid is discharged from the tip 38 of the tool 20 to adjust how much or how little squeezing pressure is applied to the bulb 98 using their hand 32 grasping the handle 22 of the tool 20 to squeeze the bulb 98. Where a greater amount of flow is desired, the bulb 98 can be squeezed harder and more rapidly to not only cause the bulb sidewall 94 to unseat a greater distance from the valve body 102 opening the valve 108 more, the application of greater squeezing pressure or force causes the compressible bulb 98 to force more fluid through the valve body 102 into the downstream conduit section 76 and out the tip 38 of the tool 20.

Figure 11:
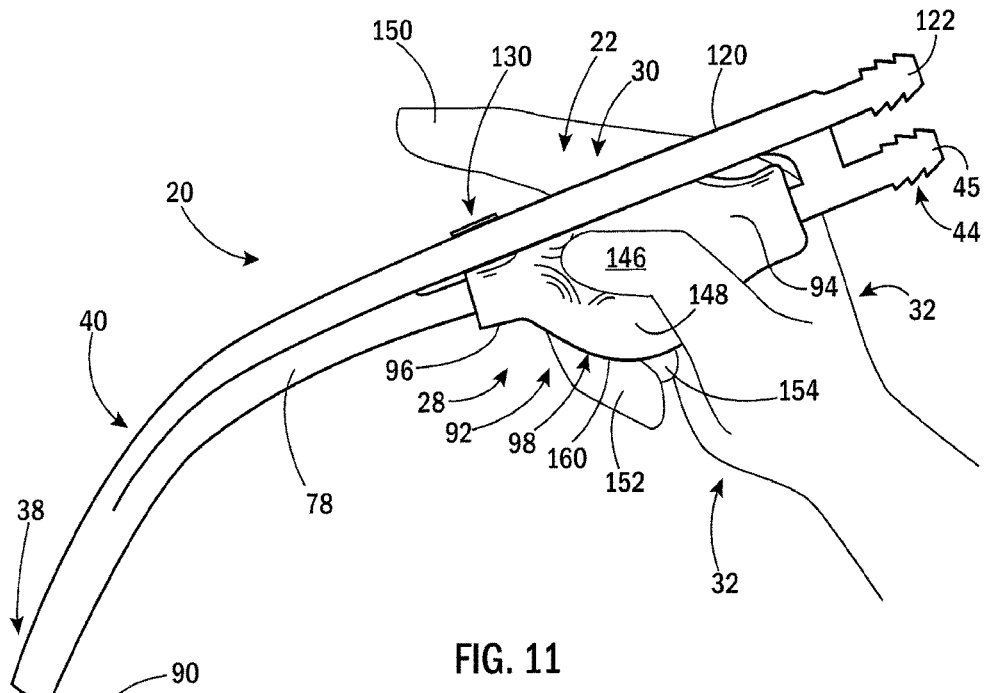
FIG. 11 is a side elevation view of the tool being grasped by a hand of a user using a pencil type grip depicting hand-held operation of the tool to discharge irrigation fluid from the tool.
Figure 12:
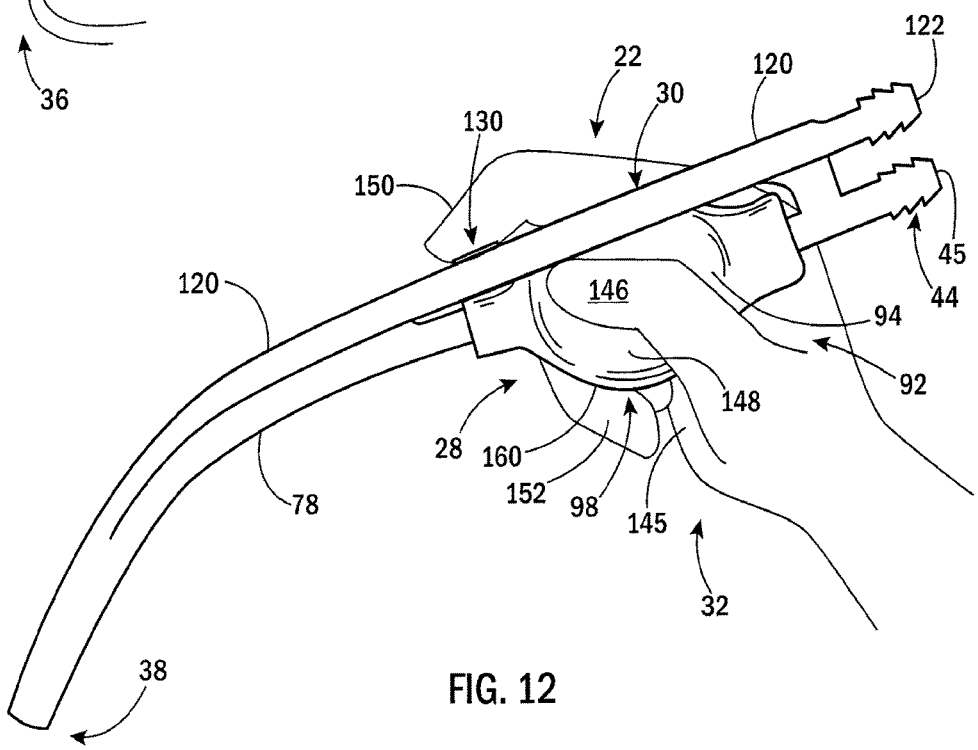
FIG. 12 is a side elevation view of the tool being grasped by a hand of a user using a pencil type grip depicting hand-held operation of an aspirator of the tool.

FIGS. 11 and 12 illustrate hand-held use and operation of the tool 20 using a single hand 32 grasping the handle 22 in a pencil type grip 166 where the hand 32 is disposed generally alongside the handgrip 28 with the thumb 146 extending along the bottom 160 and one side 148 of the bulb 98 where it can apply a squeezing pressure to the side 148 of the bulb 98 as depicted in FIG. 11 to discharge irrigation fluid from the tool 20. One or more of the fingers 150, 152, 154 or 155 can either be wrapped over or around the hand rest 30 with one or more of the other fingers 150, 152, 154 or 155 disposed alongside the opposite side 156 of the bulb 98 enabling application of a squeezing pressure to that same side 156 of the bulb 98 to discharge the irrigation fluid from the tool 20.

Where it is desired to apply suction, one or more of the fingers 150, 152, 154 or 155 and/or the thumb 146 can be moved while the hand 32 is still grasping the handle 22 to manipulate the suction flow regulating valve 130 to cause suction to be diverted to the end 38 of the wand 40. In one method of operating the aspirator 34, at least one of the fingers 150, 152, 154 or 155 and/or the thumb 146 is moved while keeping one or more of the remaining digits 146, 150, 152, 154 or 155 engaged with the handle 22 to actuate or otherwise manipulate the suction flow regulating valve 130 in a manner that causes suction to be applied at the tip 38 of the tool 20. Advantageously, a single finger, such as finger 150, 152, 154 or 155, can be moved, such as is depicted in FIGS. 11 and 12 to actuate the suction flow regulating valve 130 while also continuing to control irrigation fluid flow. For example, as is shown in FIGS. 11 and 12, a single finger 150 can be placed over one or more of the vents 132, 134, 136, and/or 138 of one preferred embodiment of a suction flow regulating valve 130 blocking one or more of the vents 132, 134, 136, and/or 138 as needed to regulate or control the amount of suction applied at the tip 38 of the tool 20.

Advantageously, a tool 20 constructed in accordance with the present invention not only enables one hand control and operation of both irrigation fluid flow and suction, it enables both to be controlled substantially simultaneously. For example, if desired, digits 146, 150, 152, 154 and 155 can be manipulated when the hand 32 is grasping the handle 22 to not only squeeze the handgrip 28 compressing the chamber 92 to cause irrigation fluid 90 to be discharged out the irrigation fluid discharge port 86 in the tip 39 of the wand 40, but also to substantially simultaneously cause suction to be applied to suction intake port 128 in the tip 38 of the wand 40 even while irrigation fluid is being discharged.

Figure 13:
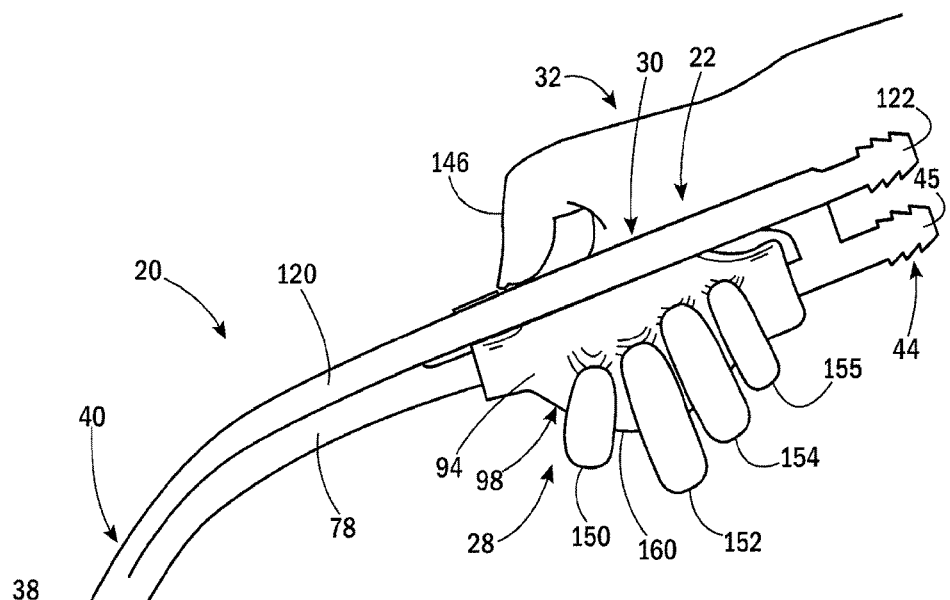
FIG. 13 is a side elevation view of the tool being grasped by a hand of a user using a golf grip depicting hand-held operation of the tool to discharge irrigation fluid from the tool.
Figure 14:
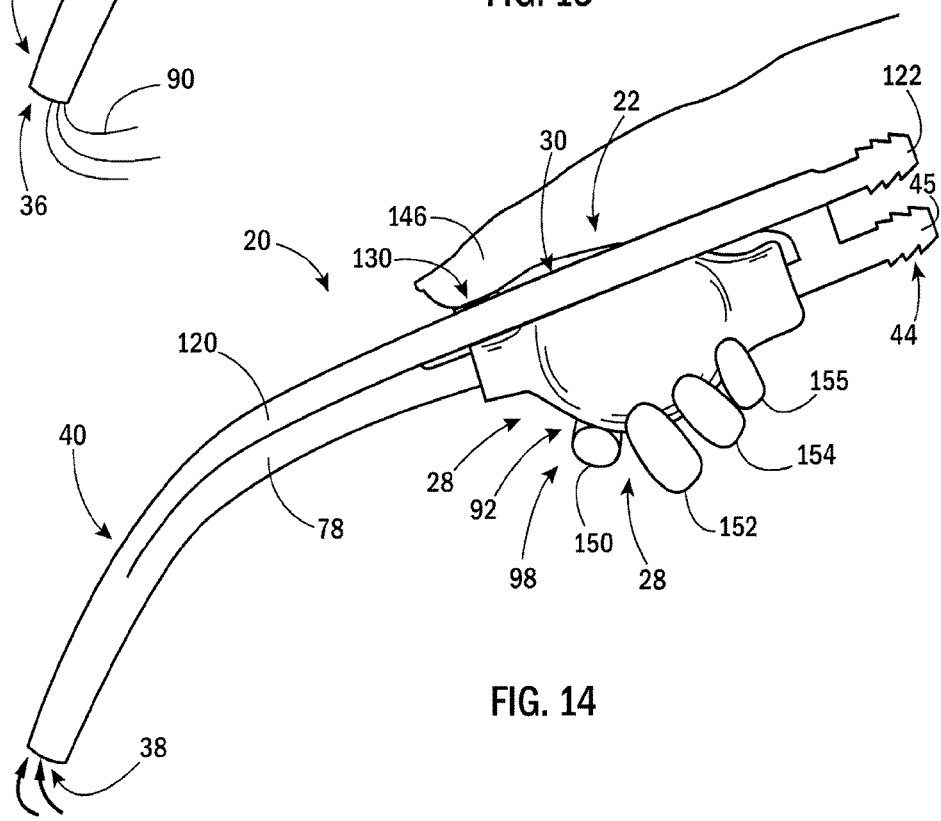
FIG. 14 is a side elevation view of the tool being grasped by a hand of a user using a golf grip depicting hand-held operation of an aspirator of the tool.

FIGS. 13 and 14 illustrate hand-held use and operation of the tool 20 using a single hand 32 grasping the handle 22 in a golf grip 168 where the palm 145 of the hand 32 is wrapped around or overlies at least part of the hand rest 30 with the thumb 146 being disposed along an adjacent part of the hand rest 30 enabling thumb operation of the suction flow regulating valve 130 while grasping the handle 22. Part of the palm 145 of the hand 32 extends along one side 156 of the bulb 98 with one or more of the fingers 150, 152, 154 or 155 wrapped underneath and around the bulb 98 so that one or more of the tips of the fingers 150, 152, 154 or 155 engage an opposite side 148 of the bulb 98 enabling the bulb 98 to be squeezed between the palm 145 and one or more of the fingers 150, 152, 154 or 155 to controllably discharge irrigation fluid from the tool 20.

As a result of the irrigation fluid reservoir 82 of the bulb 98 being in continuous fluid flow communication with the source of irrigation fluid via always open fluid coupling 65, the irrigation fluid reservoir 82 is replenished with irrigation fluid nearly as fast as it is discharged from the bulb 98. Where the source of irrigation fluid is gravity fed from an IV bag of sterile saline solution hung on a hanger at a height higher than the tool 20, irrigation fluid flows via the force of gravity from the bag back into the bulb 98 replenishing the reservoir 82.

It is also to be understood that, although the foregoing description and drawings describe and illustrate in detail one or more preferred embodiments of the present invention, to those skilled in the art to which the present invention relates, the present disclosure will suggest many modifications and constructions as well as widely differing embodiments and applications without thereby departing from the spirit and scope of the invention. The present invention, therefore, is intended to be limited only by the scope of the appended claims.

It is claimed:

1. An irrigation fluid-dispensing tool comprising:
   (a) a handle comprising (i) a hand rest, (ii) an irrigation fluid conduit, and (iii) a handgrip-receiving receptacle;
   (b) a manipulable handgrip carried by the handle and underlying the hand rest, the manipulable handgrip comprising a compressible irrigation fluid-holding chamber having a sidewall, where the compressible chamber extends alongside the hand rest and underlying the handle, the compressible chamber received in the handgrip-receiving receptacle and in fluid-flow communication with the irrigation fluid conduit, the compressible chamber defining an irrigation fluid reservoir having an internal width or diameter greater than an outer width or diameter of the irrigation fluid conduit, and the compressible chamber configured to force liquid irrigation fluid from the irrigation fluid reservoir into the irrigation fluid conduit and out of the tool when the compressible chamber is compressed at a rate of liquid irrigation fluid flow from the tool that increases in response to increasing pressure applied in compressing the compressible chamber; and
   (c) a normally-closed valve that is in operative communication with the handgrip and that comprises a valve body and a valve seat that is movable with the sidewall relative to the valve body;
   wherein the valve seat is movable with the sidewall, upon manual manipulation of the handgrip, from:
      a first position in which the valve body is seated against the valve seat to prevent irrigation fluid flow from the irrigation fluid conduit, to
      a second position in which the valve seat is spaced from the valve body to permit irrigation fluid flow from the compressible chamber.

2. The irrigation fluid-dispensing tool of claim 1, wherein the compressible chamber is urged upwardly toward the hand rest when the compressible chamber is compressed.

3. The irrigation fluid-dispensing tool of claim 1, wherein the compressible chamber is urged against the hand rest when the compressible chamber is compressed.

4. The irrigation fluid-dispensing tool of claim 1, wherein the hand rest has a suction conduit formed therein that overlies the irrigation fluid conduit, and wherein the compressible chamber is urged upwardly toward the hand rest and against part of the suction conduit when the compressible chamber is compressed.

5. The irrigation fluid-dispensing tool of claim 1, wherein the compressible chamber is compressed when the manipulable handgrip is squeezed.

6. The irrigation fluid-dispensing tool of claim 1, wherein the handle has a pair of downwardly extending arms that are spaced apart with one of the arms disposed adjacent one end of the compressible chamber, and the other one of the arms disposed adjacent an opposite end of the compressible chamber when the compressible chamber is received in the handgrip-receiving receptacle.

7. The irrigation fluid-dispensing tool of claim 1, wherein the compressible chamber abuts against the hand rest, and wherein the compressible chamber is urged against the hand rest when the manipulable handgrip is squeezed thereby compressing the compressible chamber.

8. The irrigation fluid-dispensing tool of claim 1, wherein the compressible chamber is compressed against one part of the hand rest when the manipulable handgrip is squeezed thereby compressing the compressible chamber.

9. The irrigation fluid-dispensing tool of claim 1, wherein the handle comprises a suction fluid conduit.

10. The irrigation fluid-dispensing tool of claim 9, wherein the hand rest and the suction fluid conduit overlie the compressible chamber, and wherein the compressible chamber is urged toward part of the suction fluid conduit when the manipulable handgrip is squeezed compressing the compressible chamber.

11. The irrigation fluid-dispensing tool of claim 9, wherein the suction fluid conduit is formed of the hand rest, and wherein the compressible chamber is urged against part of the suction fluid conduit when the manipulable handgrip is squeezed compressing the compressible chamber.

12. The irrigation fluid-dispensing tool of claim 9, wherein the compressible chamber is compressed against a part of the suction fluid conduit formed of the hand rest and adjacent the compressible chamber when the manipulable handgrip is squeezed compressing the compressible chamber.

13. The irrigation fluid-dispensing tool of claim 1, wherein the compressible chamber comprises an elastomeric squeeze bulb that cooperates with the normally-closed valve to provide surge flow of liquid irrigation fluid from the squeeze bulb and out of the tool when increased pressure is applied during compressing of the squeeze bulb.

14. The irrigation fluid-dispensing tool of claim 1, wherein (a) the hand rest is elongate, generally longitudinally extending, and faces outwardly in one direction, and (b) the manipulable handgrip is elongate, generally longitudinally extending, and faces outwardly in a direction opposite the hand rest.

15. The irrigation fluid-dispensing tool of claim 14, wherein the compressible chamber and the normally-closed valve are configured to enable a surge flow of liquid irrigation fluid to be forced from the irrigation fluid reservoir when the compressible chamber is compressed.

16. The irrigation fluid-dispensing tool of claim 15, wherein the compressible chamber comprises an elastomeric squeeze bulb.

17. The irrigation fluid-dispensing tool of claim 1, wherein the handgrip-receiving receptacle comprises a pair of spaced apart handgrip-mounting seats carried by the hand rest and engaging opposite ends of the compressible chamber holding the compressible chamber in place.

18. The irrigation fluid-dispensing tool of claim 17, wherein the compressible chamber is attached by the handgrip-mounting seats to the handle such that the compressible chamber is disposed between the handgrip-mounting seats.

19. The irrigation fluid-dispensing tool of claim 17, wherein the irrigation fluid conduit comprises an upstream irrigation fluid conveying passage disposed upstream of the compressible chamber and a downstream irrigation fluid conveying passage disposed downstream of the compressible chamber, and wherein one of the handgrip-mounting seats comprises a first fluid coupling in fluid flow communication with the upstream irrigation fluid conveying passage engaging one end of the compressible chamber and the other one of the handgrip-mounting seats comprises a second fluid coupling in fluid flow communication with the downstream irrigation fluid conveying passage engaging the other end of the compressible chamber.

20. The irrigation fluid-dispensing tool of claim 19, wherein each fluid coupling comprises a nipple received in a corresponding end of the compressible chamber.

21. The irrigation fluid-dispensing tool of claim 1, wherein the compressible chamber comprises an elastomeric squeeze bulb.

22. The irrigation fluid-dispensing tool of claim 1, wherein the manipulable handgrip is configured to control an amount of flow of irrigation fluid through the irrigation fluid conduit out of the tool based on an amount of pressure manually applied to the manipulable handgrip by squeezing the manipulable handgrip.

23. The irrigation fluid-dispensing tool of claim 1, wherein the normally-closed valve is configured to control an amount of flow of liquid irrigation fluid forced from the compressible chamber into the irrigation fluid conduit and out of the tool responsive to an amount of pressure applied in compressing the compressible chamber.

24. The irrigation fluid-dispensing tool of claim 1, wherein the handle has an irrigation fluid discharge port in fluid flow communication with the irrigation fluid conduit, and the handle comprises a suction fluid conduit having a suction intake port that is spaced from the irrigation fluid discharge port.

25. The irrigation fluid-dispensing tool of claim 24, wherein the handle comprises an elongate wand extending outwardly from the hand rest, and wherein the irrigation fluid conduit and the suction fluid conduit form the wand and extend to a free end of the wand with the irrigation fluid discharge port and the suction intake port formed in the free end of the wand.

26. An irrigation fluid-dispensing tool comprising:
(a) a substantially rigid handle comprising (i) a hand rest extending along a top of the tool that is adapted for engagement by a hand grasping the handle, (ii) an irrigation fluid conduit comprised of an irrigation fluid-conveying passage, and (iii) a pair of arms extending downwardly from the hand rest that are spaced apart defining a handgrip-receiving receptacle therebetween; and
(b) a manipulable handgrip carried by the handle and underlying the hand rest, the manipulable handgrip comprising a compressible sidewall forming a compressible irrigation fluid-holding chamber, wherein the compressible chamber extends alongside the hand rest and is adapted to be squeezed by the hand while grasping the handle to compress the compressible chamber, the compressible chamber having an irrigation fluid reservoir within the compressible chamber that is charged with irrigation fluid, the irrigation fluid reservoir having an internal width or diameter a plurality of times greater than an internal width or diameter of the irrigation fluid-conveying passage of the irrigation fluid conduit, the compressible chamber received in the handgrip-receiving receptacle and in fluid-flow communication with the irrigation fluid-conveying passage of the irrigation fluid conduit, the compressible chamber underlying the hand rest, and the compressible chamber forcing irrigation fluid from the irrigation fluid reservoir into the irrigation fluid-conveying passage of the irrigation fluid conduit and out of the tool when the handle is grasped and the manipulable handgrip is squeezed urging the compressible chamber against the hand rest compressing the compressible chamber; and (c) a normally-closed flow valve that is in operative communication with the handgrip and that comprises (i) a valve body and (ii) a valve seat that is movable with the sidewall in response to movement of the handgrip;

wherein the normally-closed flow valve is configured (i) to prevent irrigation fluid from exiting the tool and allow irrigation fluid to charge the irrigation fluid reservoir when the valve body is seated against the valve seat, and (ii) to allow irrigation fluid to be forced from the irrigation fluid reservoir into the irrigation fluid-conveying passage of the irrigation fluid conduit and out of the tool when the handle is grasped and the manipulable handgrip is manipulated to move the sidewall to separate the valve seat from the valve body and open the valve.

27. The irrigation fluid-dispensing tool of claim 26, wherein the compressible chamber abuts the hand rest and is urged against the hand rest when the manipulable handgrip is squeezed.

28. The irrigation fluid-dispensing tool of claim 26, wherein the compressible chamber comprises an oval or oblong elastomeric squeeze bulb and the sidewall is a curved outer sidewall inside which the irrigation fluid reservoir is disposed, and wherein a rate of irrigation fluid flow forced from the irrigation fluid reservoir increases with increasing squeezing pressure applied to the squeeze bulb when the handle is grasped and the manipulable handgrip is squeezed.

29. The irrigation fluid-dispensing tool of claim 26, wherein the handle comprises a suction fluid conduit that is formed of the hand rest of the handle and which extends alongside the compressible chamber and the irrigation fluid conduit, wherein the compressible chamber is urged against the suction fluid conduit when the handle is grasped and the manipulable handgrip is squeezed.

30. The irrigation fluid-dispensing tool of claim 29, wherein the handle has an irrigation fluid discharge port formed therein that is in fluid flow communication with the irrigation fluid conduit, the handle has a suction intake port formed therein that is in fluid flow communication with the suction fluid conduit, and the irrigation fluid discharge port is spaced from the suction fluid intake port.

31. An irrigation fluid-dispensing tool comprising:
(a) a handle comprising (i) a hand rest, (ii) an elongate suction fluid conduit formed therein that is formed of the hand rest, (iii) an elongate irrigation fluid conduit formed therein that underlies the suction fluid conduit, and (iv) a pair of downwardly extending arms that are spaced apart defining a handgrip-receiving receptacle therebetween; and
(b) a manipulable handgrip carried by the handle and disposed underneath the hand rest, the manipulable handgrip comprising a sidewall that moves upon manipulation of the handgrip and forms a surface of a squeeze bulb extending alongside and underlying the hand rest and part of the suction fluid conduit, the squeeze bulb received in the handgrip-receiving receptacle and in fluid-flow communication with the irrigation fluid conduit, the squeeze bulb having a width or diameter greater than a width or diameter of the irrigation fluid conduit, and the squeeze bulb configured to discharge irrigation fluid into the irrigation fluid conduit and out of the tool when the squeeze bulb is squeezed; and
(c) a normally-closed irrigation fluid flow valve that is in operative communication with the handgrip and that comprises (i) a valve body and (ii) a valve seat that moves with the sidewall,
wherein the valve body is seated against the valve seat in an absence of manual manipulation of the handgrip;
wherein the valve seat is spaced away from the valve body to enable irrigation fluid to flow through the irrigation fluid conduit upon manual manipulation of the handgrip in a manner that moves the sidewall and the valve seat; and
wherein the normally-closed irrigation fluid flow valve prevents irrigation fluid flow out of the irrigation fluid conduit and allows charging of the squeeze bulb when the valve body is seated against the valve seat, and allows discharge of irrigation fluid from the squeeze bulb into the irrigation fluid conduit upon manipulation of the handgrip and squeezing of the squeeze bulb.

32. The irrigation fluid-dispensing tool of claim 31, comprising an elongate wand extending outwardly from the hand rest, the wand having (a) an irrigation fluid discharge port formed therein that is in fluid flow communication with the irrigation fluid conduit, and (b) a suction intake port formed therein that is in fluid flow communication with the suction fluid conduit, and wherein the irrigation fluid discharge port is spaced from the suction fluid intake port.

33. An irrigation fluid-dispensing tool comprising:
(a) a substantially rigid handle comprising (i) a hand rest extending along a top of the tool that is adapted for engagement by a hand grasping the handle, (ii) an irrigation fluid conduit comprised of an irrigation fluid-conveying passage, and (iii) a pair of arms extending downwardly from the hand rest that are spaced apart defining a handgrip-receiving receptacle therebetween; and
(b) a manipulable handgrip comprising a compressible sidewall forming a compressible irrigation fluid-holding chamber, wherein the compressible chamber extends alongside the hand rest and is adapted to be squeezed by manual manipulation of the handgrip while grasping the handle to compress the compressible chamber, the compressible chamber having an irrigation fluid reservoir within the compressible chamber that is charged with irrigation fluid, the irrigation fluid reservoir having an internal width or diameter a plurality of times greater than an internal width or diameter of the irrigation fluid-conveying passage of the irrigation fluid conduit, the compressible chamber received in the handgrip-receiving receptacle and in fluid-flow communication with the irrigation fluid-conveying passage of the irrigation fluid conduit, the compressible chamber underlying the hand rest, and the compressible chamber forcing irrigation fluid from the irrigation fluid reservoir into the irrigation fluid-conveying passage of the irrigation fluid conduit and out of the tool when the handle is grasped and the manipulable handgrip is squeezed urging the compressible chamber against the hand rest compressing the compressible chamber; and
(c) a normally-closed flow valve that is in operative communication with the handgrip and that comprises (i) a valve body and (ii) a valve seat that is movable with the sidewall in response to movement of the handgrip;

wherein the normally-closed flow valve is configured (i) to prevent irrigation fluid from exiting the tool and allow irrigation fluid to charge the irrigation fluid reservoir when the valve body is seated against the valve seat, and (ii) to allow irrigation fluid to be forced from the irrigation fluid reservoir into the irrigation fluid-conveying passage of the irrigation fluid conduit and out of the tool when the handle is grasped and the manipulable handgrip is manipulated to move the sidewall to separate the valve seat from the valve body and open the valve.

* * * * *